(12) United States Patent
Weisel

(10) Patent No.: US 9,549,548 B2
(45) Date of Patent: Jan. 24, 2017

(54) METHOD FOR PROVIDING A TEAT DIP COMPOSITION

(71) Applicant: Jeffrey A. Weisel, North Lawrence, OH (US)

(72) Inventor: Jeffrey A. Weisel, North Lawrence, OH (US)

( * ) Notice: Subject to any disclaimer, the term of this patent is extended or adjusted under 35 U.S.C. 154(b) by 0 days.

(21) Appl. No.: 14/815,969

(22) Filed: Aug. 1, 2015

(65) Prior Publication Data
US 2015/0335024 A1    Nov. 26, 2015

Related U.S. Application Data

(63) Continuation of application No. 14/361,020, filed as application No. PCT/US2012/066779 on Nov. 28, 2012, now abandoned.

(60) Provisional application No. 61/563,888, filed on Nov. 28, 2011.

(51) Int. Cl.
| | |
|---|---|
| *A61K 8/20* | (2006.01) |
| *A61K 8/34* | (2006.01) |
| *A01N 59/00* | (2006.01) |
| *A01N 25/32* | (2006.01) |
| *A61K 31/045* | (2006.01) |
| *A61K 31/047* | (2006.01) |
| *A61K 33/00* | (2006.01) |
| *A01N 31/02* | (2006.01) |
| *A61Q 17/00* | (2006.01) |
| *A61Q 19/00* | (2006.01) |

(52) U.S. Cl.
CPC ............... *A01N 25/32* (2013.01); *A01N 31/02* (2013.01); *A01N 59/00* (2013.01); *A23K 20/147* (2016.05); *A23K 20/158* (2016.05); *A23K 50/10* (2016.05); *A61K 8/20* (2013.01); *A61K 8/345* (2013.01); *A61K 31/045* (2013.01); *A61K 31/047* (2013.01); *A61K 33/00* (2013.01); *A61K 2800/30* (2013.01); *A61Q 17/005* (2013.01); *A61Q 19/00* (2013.01)

(58) Field of Classification Search
USPC ........................................................... 424/49
See application file for complete search history.

(56) References Cited

U.S. PATENT DOCUMENTS

| | | | | |
|---|---|---|---|---|
| 3,826,826 | A * | 7/1974 | Cantor ................... | A61K 33/14 424/605 |
| 4,199,602 | A * | 4/1980 | Lentsch ............... | A61K 31/195 514/727 |
| 5,685,262 | A * | 11/1997 | Stevenson ................. | A01J 7/04 119/651 |
| 6,586,477 | B1 * | 7/2003 | Schattner ............... | A01N 31/08 514/731 |
| 2001/0036482 | A1 * | 11/2001 | Fredell ................... | A61K 33/18 424/667 |
| 2005/0031705 | A1 * | 2/2005 | Tyndall ................ | A61K 9/0017 424/616 |
| 2009/0324514 | A1 * | 12/2009 | Awad ..................... | A01N 31/02 424/49 |
| 2010/0267662 | A1 * | 10/2010 | Fielder ................. | A61K 36/899 514/54 |
| 2012/0172437 | A1 * | 7/2012 | Kraus ................... | C07C 407/00 514/557 |

\* cited by examiner

*Primary Examiner* — Walter Webb
(74) *Attorney, Agent, or Firm* — Zollinger & Burleson Ltd.

(57) ABSTRACT

An aqueous teat dip composition includes significant amounts of glycerin and preferably ethanol and has a pH of at least 8.5. The aqueous teat dip composition can be provided by a method that involves delivering a basic concentrate to a site where dairy animals are located where the concentrate is mixed with water before the pH of the resulting solution is upwardly adjusted. The basic concentrate can be a byproduct of a biofuel refining process.

14 Claims, No Drawings

METHOD FOR PROVIDING A TEAT DIP COMPOSITION

CROSS-REFERENCE TO RELATED APPLICATIONS

This application is a continuation of U.S. patent application Ser. No. 14/361,020, which was a national stage entry of international application no. PCT/US2012/066779, filed 28 Nov. 2012, which claims the benefit of U.S. patent appl. No. 61/563,888, filed 28 Nov. 2011, the disclosures of which are incorporated herein by reference.

BACKGROUND INFORMATION

Most so-called biofuels are transesterification products of any of a variety of animal fats and vegetable oils. When the oil or fat is exposed to an alcohol (typically methanol) under appropriate catalytic conditions, the fatty acids can cleave from the glycerol radical and react with the alcohol to form fatty acid esters. The transesterification reaction significantly reduces the viscosity of the oil. For more information on the manufacture and properties of such biofuels, the interested reader is directed to any of a variety of overviews such as, e.g., M. Graboski et al., "Combustion of Fat and Vegetable Oil Derived Fuels in Diesel Engines," *Prog. Energy Combust. Sci.*, vol. 24, pp. 125-64 (1998, Elsevier).

Most biofuel is refined using a process employing large amounts of water to remove the strong bases that catalyze the transesterification process. The resulting wastewater, absent some type of neutralization, is quite caustic and can cause problems if discharged directly into municipal treatment systems. One refining process that avoids this concern is described in U.S. Patent Publ. No. 2010/0199549 (Harnar et al.), which eliminates the need for water washing of the raw fuel product.

Another concern for biofuel refiners is the glycerin (glycerol) byproduct. While a viable market for raw glycerin exists, the methanol used in most biodiesel refining processes complicates its use in many of the available applications, e.g., pharmaceuticals, personal care products and food additives. Perhaps not coincidentally, these are the applications where glycerin often commands the highest prices. In agricultural settings, glycerin finds use as a feed additive and as an emollient in, for example, teat dips.

A teat dip is an antimicrobial composition used to cleanse and sanitize the teat area before and after milking; bacteria including *Staphylococcus aureus, Streptococcus agalactiae, Mycoplasma bovis*, and *Corynebacterium bovis* are commonly encountered in dairy farming operations. Application of such a composition is a significant part of the recommended program to reduce or control mastitis. Teat dips must have antimicrobial properties, have low human toxicity (because the teat dip can enter into a dairy product during collection of milk) and have low environmental impact when discharged into the waste stream produced by the area in which dairy animals are milked, often referred to as a milking parlor.

Optimally, a teat dip will condition the teat tissue at the same time that it is providing its sanitizing effects. A typical emollient is glycerin, originating either as a byproduct of corn ethanol plants or from petroleum.

Teat dips commonly are distributed in pre-mixed form from warehousing and supply plants to dairy farms. The vast majority of commercial teat dips are based on iodine, sometimes provided free in solution but more commonly complexed with, e.g., polyvinylpyrrolidone (Povidone). Exemplary formulations typically include large amounts (e.g., 91-95% (by wt.)) water, small amounts of acid and/or base, 2-4% (by wt.) complexed iodine, and 2-4% (by wt.) glycerin; such formulations typically have a pH of 4-5 and can be modified through the addition of viscosity modifiers, surfactants, stabilizers, additional antimicrobials (e.g., chlorhexidine, quaternary ammonium, dodecyl benzene sulfonic acid, nisin, hydrogen peroxide, etc.), and the like. The amount of free iodine in these types of teat dips typically varies from ~0.15 to 3%, with lesser amounts (e.g., 0.18%) becoming more common so as to reduce teat irritation and to lessen the risk of iodine residues in milk; processing plants have notified producers that iodine needs to be kept out of the milk stream because it causes problems with processing and yields.

Some products currently used as teat dips actually increase disease due to a combination of poor formulation (free iodine is not available in lethal doses) and how the teat dip is used, i.e., as a viscous liquid (film) that stays on the teat and udder after milking, thereby providing a medium to attract and retain bacteria-laden solids such as feces. To complicate matters, the glycerin emollient can act as a food source for any bacteria that is trapped in or on the viscous dip or its dried residue. Applying more teat dip prior to the next milking can merely trap the bacteria in the older, still present layer present on the udder and teat.

SUMMARY

In one aspect is provided an aqueous teat dip composition that includes significant amounts of ethanol and glycerin and that has a pH>8.5, typically pH>9 and even more typically pH>9.5. In use, the temperature of the teat dip composition preferably is above 32° C. (~90° F.), more preferably above 35° C. (~95° F.), and even more preferably from 37° to 54° C. (~100° to ~130° F.).

In another aspect is provided a method of providing the foregoing aqueous teat dip composition. The method involves delivering a basic (caustic) composition to a site where dairy animals are located, with the composition including no more than 10% (by vol.), preferably no more than 5% (by vol.), and even more preferably no more than 2% (by vol.) water. At the site, the composition is mixed with water and the pH of the resulting solution is adjusted to at least ~8.5, typically ~9 and even more typically ~9.5. In some embodiments, the water added can be at a temperature of from 35° to 60° C. (~95° to ~140° F.), commonly from 37° to 57° C. (~100° to ~135° F.), and preferably from 43° to 54° C. (~110° to ~130° F.). The basic composition can be a byproduct of a biofuel refining process.

In a further aspect is provided a feed supplement that includes significant amounts of ethanol and glycerin. The feed supplement is basic (caustic) and includes at least 10% (by wt.) soluble protein as a percentage of total crude protein. Advantageously, the feed supplement can be obtained as an untreated, unrefined byproduct of a biofuel refining process.

In a still further aspect is a method of disposing of the glycerin byproduct of a biofuel refining process. Ethanol and glycerin constitute the primary components of the byproduct composition. The composition is delivered to a site where dairy animals are located, where it can be used directly as a feed additive (or supplement) or mixed with water and a small amount of a moderate or strong base so as to provide a basic (caustic) teat dip, i.e., one with a pH>8.5, typically pH>9 and even more typically pH>9.5. Advantageously, the byproduct contains little or no methanol.

Other aspects of the invention are set forth in the more detailed description which follows. The relevant portion(s) of all patent documents or publications mentioned herein-throughout are incorporated by reference.

DETAILED DESCRIPTION OF ILLUSTRATIVE EMBODIMENTS

Milking parlors operate at a fast pace, with dairy animals being kept in the milking parlor for as little time as possible. A teat dip often is applied less than 90 seconds, sometimes as little as 10 seconds, prior to attachment of a milking unit. Free iodine needs an extended contact time for it to kill microbes and, when combined with the presence of the polymeric binder and emollients, that contact time goes up. Higher activities (i.e., shorter contact times) are desirable in view of the pace at which milking parlors are operated.

Additionally, the rubber articles attached to a teat for removal of milk are negatively affected by the acidic and oxidizing compositions commonly employed as teat dips. A teat dip composition that is not as hard on milking equipment and articles also is desirable.

Sodium hypochlorite solutions have been used both as pre- and post-milking teat dips. Hypochlorite is a strong oxidizing agent; to avoid damaging teat skin, commercial products (i.e., laundry bleach), which typically contain ~6.0-6.25% hypochlorite, are diluted with water so as to reduce the concentration of hypochlorite ion to 4.0%. Such products are caustic, with a pH typically on the order of 10 to 12.

Two issues complicate or interfere with a broader use of hypochlorite solutions. The first is the relatively transient nature of the hypochlorite ion, which complicates the manufacture of the teat dip solution too far in advance of its use. Additionally, additives such as emollients are not present in commercial bleach products and, in fact, cannot be incorporated easily. A hypochlorite-based teat dip that can condition the teat at the same time that it is disinfecting it remains desirable.

The present aqueous teat dip composition is intended to be caustic. In use, it has a pH of at least 8.5, commonly at least ~9, and even more typically at least ~9.5; in some embodiments, the pH of the teat dip composition can range from 8.5 to 10.5, commonly from 9.0 to 10.3, typically from 9.2 to 10.0, and even more typically from 9.3 to 9.8. Hereinthroughout, pH measurements are those provided by a properly calibrated pH meter such as, for example, a HM Digital™ PH-200 pH meter (HM Digital, Inc.; Culver City, Calif.).

Such high pH values require the use of large amounts of a moderately strong base such as ammonia or laundry bleach or moderate amounts of a strong base such as an Group I metal hydroxide (e.g., NaOH or KOH). However, employing the biofuel byproduct described below, the amount of separately added strong base can be reduced (or even avoided altogether), and the amount of moderately strong base can be greatly reduced.

The teat dip composition preferably includes glycerin as an emollient, most preferably glycerin derived from plants, e.g., corn. The amount of glycerin added need not be great, with no more than 5 parts (by vol.) based on 100 parts water providing satisfactory results. The amount of glycerin commonly ranges from ~1 to ~15 parts (by vol.), more commonly from ~1.2 to ~12, typically from ~1.5 to ~10, more typically from ~1.7 to ~7.5, and most typically from ~2 to ~4 parts (by vol.) based on 100 parts water.

Although the temperature of the teat dip composition at the time of application can vary widely, additional benefits have been seen when the composition is applied at a temperature of at least 32° C. (~90° F.), preferably above 35° C. (95° F.), and even more preferably from 37° to 54° C. (~100° to ~130° F.). Such temperatures can be achieved by mixing the base and glycerin with water provided at a temperature of from 35° to 60° C. (95° to ~140° F.), commonly from 37° to 57° C. (~100° to ~135° F.), and preferably from 43° to 54° C. (~110° to ~130° F.).

An exemplary and beneficial manner of providing the teat dip composition is as a concentrate that can be added to water (or vice versa) at the time of intended use. This reduces the amount of packaging needed to hold and store the non-water ingredients and the amount of energy needed for delivery of the active ingredients to the site of use.

An exemplary concentrate is caustic, with a pH of at least 8.5, preferably at least 9.0 and more preferably at least 9.5, and optionally includes an emollient such as glycerin. Such a concentrate can be prepared by adding a strong base (e.g., lye) to a glycerin-containing composition. Where an appropriate stabilizer is included, hypochlorite ion also can be present in the concentrate, although addition of bleach as a separate component can be preferred for a variety of reasons (including transportation regulations). The concentrate also can contain any of a variety of additives or adjuvants including emulsifiers, detergents, fragrances, colorants, and the like (particular those derived from natural sources, e.g., juice or extract from a citrus fruit such as lemon), although coalescents and film-forming materials (e.g., polyvinylpyrrolidone) preferably are omitted. Additionally, the amount of water present in the concentrate advantageously can be kept very low so as to minimize weight, thereby reducing transportation costs. Further, the amount of iodine in the teat dip composition need not be significant, i.e., can be well below 0.1% (by wt.) or even 0.01% (by wt.), thereby eliminating the concern of processors regarding the amount of iodine entering the milk supply from the teat dip.

Notwithstanding the foregoing, a preferred method of providing it is as a byproduct from a biofuel refining process; a useful refining process is described below. When such a byproduct is used as a concentrate, it preferably includes a significant amount of ethanol in addition to glycerin; for present purposes, a significant amount is at least 5% (by vol.), commonly at least ~7.5% (by vol.), more commonly at least ~10% (by vol.), typically at least about 12.5% (by vol.), and more typically at least about 15% (by vol.). Some byproduct concentrates can include up to 20% (by vol.) or even 25% (by vol.) ethanol, although the amount of ethanol present preferably does not exceed 30% (by vol.).

Most biofuel refining processes employ methanol in the transesterification step. When glycerin is intended for use in a dairy farm setting, the presence of even a small amount of methanol is problematic. Accordingly, a concentrate that contains less than 0.5% (by wt.), preferably less than 0.1% (by wt.), more preferably less than 0.05% (by wt.), even more preferably less than 0.01% (by wt.), still more preferably less than 0.005% (by wt.), even still more preferably less than 0.001% (by wt.), and most preferably less than 0.0005% (by wt.) methanol.

Additionally, the biofuel refining byproduct typically contains very little water, has a moderately high pH (typically at least 9.5), and a moderate amount of sodium or potassium ions (from the Group I or II metal hydroxide base used as a catalyst in the refining process).

An advantage of the biofuel refining byproduct as a concentrate is its non-toxic nature. In fact, analysis by an independent testing lab confirmed that the byproduct concentrate is safe to use as a feed supplement. It has a high level of soluble protein (as a result of the vegetable oil used in the refining process, described below) and few if any detrimental ingredients. Obviously, where a byproduct concentrate contains a significant amount of ethanol, the amount of concentrate used as a feed supplement needs to be moderated, i.e., diluted prior to addition or used in small amounts.

Where the biofuel refining product is used as a concentrate, a teat dip composition can be prepared by adding, per 100 parts (by vol.) water, from ~2 to ~5 parts (by vol.) concentrate and then adding a sufficient amount of moderately strong base (e.g., one that includes $NH_4^+$ or $ClO^-$ ions) to raise the pH of the overall teat dip composition to at least ~10, preferably from 10 to 10.5; because the hypochlorite ion is an oxidizer, bleach is preferred over ammonia as a component in the teat dip composition. Stabilizers and other adjuvants, if desired, can be added at any point in the mixing process.

Where household bleach (6-6.25% strength) is used as the pH adjusting liquid, depending on the acidity/alkalinity of the water source, from 9-18 parts (by vol.), typically from 10-16 parts (by vol.), can be added. A teat dip composition that includes bleach preferably is used within a few hours of mixing due to the tendency of the hypochlorite ion to degrade.

Although the order of addition is not believed to be critical, a recommended recipe is to add concentrate to a small volume of water and then add more water before finally adding the pH adjusting liquid. More water then can be added to achieve the desired volume of teat dip composition. As indicated previously, the pH of the composition typically is at least ~10, preferably from 10 to 10.5, which can be confirmed in a variety of ways including, for example, testing with a pH meter.

A teat dip composition according to the present invention has a relatively low viscosity, i.e., not significantly different than that of water. This permits the composition to be applied easily and, when it does not include a coalescent and film-forming agent, to easily evaporate and/or drip off the udder and teat. The fact that the teat dip does not remain caked on the udder and teat means that it cannot act to attract and hold bacteria present in barns, farm fields and manure.

Further, the present teat dip composition has been found to have cleansing properties. Application of the composition to an udder has been observed to loosen and remove solids such as dirt and feces. This is believed to be due to the relatively high levels of glycerin and ethanol, as well as the absence of a coalescent/film-forming material that can attract and hold such undesirable materials.

As indicated above, an exemplary, even preferred, teat dip concentrate is the byproduct of a certain type of biofuel refining process. An example of such a refining process can be found in U.S. Pat. Publ. No. 2010/0199549 A1. A brief description of the first part of that refining process is provided here for ease of reference.

The refining process gives preference to highly pure vegetable oils, more preferably to food-grade materials, examples of which include corn, linseed, peanut and soybean oils. For purposes of the present invention, use of food-grade materials has the advantage helps to ensure the safe nature of the ultimate byproduct in conjunction with dairy animal-related uses.

A preferred starting material is a food-grade vegetable oil; particularly preferred are those that are refined, bleached, and deodorized (RBD). The remainder of this description is based on an RBD soybean oil.

The other reagent in transesterification reactions is an alcohol. Although the vast majority of biofuels being made employ methanol as a reagent (with the European Biodiesel Board even mandating the use of methanol where a producer wishes to have its product certified as a biodiesel fuel), that refining process employs higher alcohols, specifically one or more $C_2$-$C_6$ alcohols. Each alcohol employed preferably is aliphatic, and more preferably has the general formula $C_nH_{2n+1}OH$ where $2 \leq n \leq 6$. The most preferred alcohol is absolute ethanol (denatured by means of a hydrocarbon liquid, e.g., gasoline).

Reaction between the alcohol(s) and triglyceride(s) is catalyzed by both acids and bases; for present purposes, processes that employ a strong base are preferred. Typically, no more than ~1% (by wt.) catalyst is required. The catalyst can be delivered in some or all of the alcohol(s) by dissolving a strong base, e.g., NaOH or KOH, in the alcohol(s) prior to delivery of the alcohol(s) to the reaction vessel. If desired, the catalyst solution can be added stepwise, i.e., through the addition of sequential aliquots followed by mixing or agitation.

An excess of alcohol preferably is employed during the transesterification; the amount typically ranges from ~25 to ~200%, preferably from ~50 to ~150%, more preferably from ~70 to ~130%, even more preferably from ~80 to ~120%, and most preferably at least ~100% excess (all by volume). To a certain extent, the stoichiometric excess of alcohol can be varied somewhat so as to create fuel compositions with slightly different properties.

Despite the aforementioned preference for using an excess of alcohol during the manufacture and refining steps, at least some of the benefits might be able to be achieved by post-manufacture addition of alcohol during or after refining.

Where conventional agitation techniques (e.g., a circulating pump) are employed, the transesterification reaction generally proceeds to completion in a few hours at 20°-25° C. The transesterification reaction can be expedited with relatively gentle heating although this certainly is not required.

The transesterification reaction results in glycerol and other glycerin byproducts. Depending on the identity, nature, and purity of the reagents, the glycerol in the reaction vessel can separate on its own, can partially separate, or separate only minimally. For example, where high purity reagents are used, glycerol and derivatives typically separate from the alkyl ester/ethanol phase in a few hours (e.g., 4-12 hours) after agitation is ceased. However, where a less refined starting material is employed, addition of more alcohol (e.g., up to ~20% additional alcohol) and/or additional time can be needed to achieve the desired level of separation. The alcohol added for separation purposes need not be the same as that used in the reaction, although the use of methanol is preferably avoided.

The glycerol phase, which is heavier than the alkyl ester/alcohol phase and thus separates to the bottom of the reaction vessel, advantageously is quite basic, i.e., pH of at least 9. Because of the excess amount of alcohol used during the transesterification reaction, the glycerol layer also contains 5 to 30% (by vol.), typically 10 to 25% (by vol.), alcohol but preferably is free of methanol. This biofuel refining process byproduct is an example of that which can be used as or in a previously described feed supplement or teat dip concentrate.

Terms and phrases used in this description are believed to assist in the understanding of the composition and processes of the present invention. However, no unnecessary limitations are to be implied from the brief, concise description of illustrative embodiments provided.

That which is claimed is:

1. A method for making a composition useful for treating the teat area of dairy animals, said method comprising:
   a) providing a concentrate that comprises glycerin, an alcohol, and no more than 10% by volume water based on the total volume of said concentrate, said concentrate having a pH of at least 9.0;
   b) combining from about 2 to about 5 parts by volume of said concentrate with 100 parts by volume water so as to provide an initial mixture; and
   c) upwardly adjusting the pH of said initial mixture of a base that comprises $NH_4^+$ or $ClO^-$ ions, thereby providing said composition,
said composition having a pH of at least about 9.

2. The method of claim 1 wherein said composition has a pH of at least about 9.5.

3. The method of claim 1 wherein said composition has a pH of at least 10.

4. The method of claim 3 wherein said composition has a pH of from 10 to 10.5.

5. The method of claim 1 wherein said composition has a pH of from 9.0 to 10.3.

6. The method of claim 1 wherein said concentrate further comprises a Group I metal ion.

7. The method of claim 1 wherein said concentrate comprises sufficient glycerin so as to provide said composition with from 1 to 15% by volume glycerin.

8. The method of claim 7 wherein said concentrate comprises sufficient glycerin so as to provide said composition with from 2 to 4% by volume glycerin.

9. The method of claim 1 wherein said composition comprises less than 0.1% by weight iodine.

10. The method of claim 9 wherein said composition comprises less than 0.01% by weight iodine.

11. The method of claim 1 wherein said concentrate comprises no more than 5% by volume water.

12. The method of claim 11 wherein said concentrate comprises no more than 2% by volume water.

13. The method of claim 1 wherein said concentrate is a biofuel refining process byproduct.

14. The method of claim 13 wherein said concentrate has a pH of at least 9.5.

* * * * *